(12) United States Patent
Friedland et al.

(10) Patent No.: US 8,784,341 B2
(45) Date of Patent: Jul. 22, 2014

(54) TONGUE DEPRESSOR WITH A FORCE/PRESSURE SENSING ELEMENT

(76) Inventors: Eric Mitchell Friedland, Livingston, NJ (US); Mark Shaffer Annett, Livingston, NJ (US)

( * ) Notice: Subject to any disclaimer, the term of this patent is extended or adjusted under 35 U.S.C. 154(b) by 226 days.

(21) Appl. No.: 13/013,001

(22) Filed: Jan. 25, 2011

(65) Prior Publication Data

US 2011/0190666 A1   Aug. 4, 2011

Related U.S. Application Data

(60) Provisional application No. 61/299,956, filed on Jan. 30, 2010.

(51) Int. Cl.
*A61B 5/103* (2006.01)
*A61B 5/117* (2006.01)

(52) U.S. Cl.
USPC .......................................... 600/590; 600/587

(58) Field of Classification Search
USPC .................................................. 600/587, 590
See application file for complete search history.

(56) References Cited

U.S. PATENT DOCUMENTS

| | | | |
|---|---|---|---|
| 4,585,012 A | 4/1986 | Rumburg | |
| 4,697,601 A | 10/1987 | Durkee et al. | |
| 4,867,697 A * | 9/1989 | Borges | 439/265 |
| 4,928,707 A * | 5/1990 | Schiffman et al. | 600/587 |
| 5,070,859 A * | 12/1991 | Waldvogel | 600/185 |
| 5,119,832 A | 6/1992 | Xavier | |
| 5,609,161 A | 3/1997 | Tura et al. | |
| 5,954,673 A | 9/1999 | Staehlin et al. | |
| 6,050,961 A | 4/2000 | Arnold | |
| 6,190,335 B1 | 2/2001 | Howard et al. | |
| 6,272,936 B1 * | 8/2001 | Oreper et al. | 73/862.621 |
| 6,511,411 B1 | 1/2003 | Brown | |
| 6,702,765 B2 | 3/2004 | Robbins et al. | |
| 7,238,145 B2 | 7/2007 | Robbins et al. | |
| 2003/0078521 A1 | 4/2003 | Robbins et al. | |
| 2008/0183107 A1 | 7/2008 | Miller et al. | |
| 2010/0022918 A1* | 1/2010 | Fujie et al. | 600/587 |
| 2010/0184566 A1 | 7/2010 | Munehiro | |
| 2010/0222706 A1 | 9/2010 | Miyahara et al. | |

FOREIGN PATENT DOCUMENTS

JP      2007 202922 A      8/2007

* cited by examiner

*Primary Examiner* — Brian Szmal
*Assistant Examiner* — Megan Leedy (57) ABSTRACT

A body force measurement system for both assessment and therapeutic usage comprising a non-rigid tongue depressor with a force sensing element attached to it and a means of converting the force sensed into quantifiable data. The system provides convenient method for making body force measurements consistent with current clinical practice and without the need for a fixed registration point.

10 Claims, 6 Drawing Sheets

TONGUE DEPRESSOR WITH A FORCE/PRESSURE SENSING ELEMENT

CROSS-REFERENCE TO RELATED APPLICATIONS

This application claims the benefit of U.S. Provisional Patent Application No. 61/299,956, filed 30 Jan. 2010.

STATEMENT REGARDING FEDERALLY SPONSORED RESEARCH OR DEVELOPMENT

Not Applicable

REFERENCE TO SEQUENCE LISTING, A TABLE, OR A COMPUTER PROGRAM LISTING COMPACT DISK APPENDIX

Not Applicable

BACKGROUND

1. Field

This application relates to the field of body force measurement, specifically to those utilized in the medical and therapeutic setting and more specifically to those generated by the teeth lips and tongue.

2. Prior Art

Speech, language, and swallowing difficulties can result from a variety of causes including stroke, brain injury/deterioration, developmental delays/disorders, learning disabilities, cerebral palsy, cleft palate, voice pathology, mental retardation, hearing loss, or emotional problems and the difficulties can be either congenital, developmental, or acquired.

Speech-language pathologists assess, diagnose, treat, and help to prevent disorders related to speech, language, cognitive-communication, voice, swallowing, and fluency. Treatment modalities may include range of motion and isometric exercises of the oral mechanisms. These techniques facilitate coordination and strength of the speech and swallowing muscles. Labial (relating to the lips) and lingual (pertaining to the tongue) isometric exercises are completed with use of a tongue depressor. Strengthening is accomplished by repetitive isometric force against the tongue depressor. This is completed in the lateral directions (side to side), protrusion/extension (out), upward and downward directions. Labial isometric exercises can also include completion of a strong labial seal on the tongue depressor.

Diagnostic baseline data and therapeutic progress is measured by a subjective assessment of force against the tongue depressor by the Speech Pathologist. This measurement technique is very inaccurate as the perception of the exerted force is inexact and varies from session to session. Furthermore, from session to session patients may be treated by different Speech Pathologists with the outcome that their overall progress will be subjectively assessed by several clinicians.

Although several devices have been patented to aid in the assessment and treatment by speech-language pathologists all of these devices require the clinician to modify their clinical practice. One of the earliest tools was specified by Rumburg, in U.S. Pat. No. 4,585,012. In this device, a chin rest is utilized for patient registration (the physical connection between the patient and the fixed point against which measurements are taken). Once the patient is registered to the device, the patient pushes against a blade (presumably a tongue depressor) causing the blade to bend against a pivot point. Rather than directly measuring the applied force, it is indirectly measured by measuring the amount of bending of the blade with a dial caliper. Not only is this indirect measurement subject to variability due to variations in the blade, variations in anatomy from person to person will cause their tongue to contact at different points on the blade and therefore the system would not provide accurate measurements between patients.

The potential to obtain a reliable measure of tongue strength in multiple directions was first described by Durke et. al. in U.S. Pat. No. 4,697,601 back in 1987. The independent claim is for a device that uses strain gauges to measure tongue force simultaneously in three directions by having the individual push against a tongue cup. However, the device is essentially non-functional without its dependent claim of further including a bifurcated tooth plate fastened to the device, which serves as a means of patient registration. Otherwise, given the "rigid" nature of the measurement system, if the therapist were simply to try and hold the device in place while the patient pushes against it, the therapist influence could easily be as great, or greater, than the effect trying to be measured. In fact, without the bifurcated tooth plate, a subjective assessment by an experienced clinician is probably far more accurate than an unregistered "rigid" mechanical device held in a clinician's hand.

Patient registration is actually one of the primary differentiation points between devices designed to measure tongue strength and Masahiko Wakumoto et al, U.S. Pat. No. 6,511,441, even goes so far as to attach electrodes directly to the roof of patient's mouth. However, the most common method of patient registration is to use a mouth piece. For instance, both Staehlin et al, U.S. Pat. No. 5,954,973 and Robbins et. al., U.S. Pat. No. 6,702,765 employ a mouth piece that substantially conforms to the patient's anatomy as a means of patient registration. These customized mouth pieces are expensive to produce and expensive and time consuming for the therapist to employ in daily practice.

At the other end of the spectrum is the IOWA Oral Performance Instrument, Robin et. al. U.S. Pat. No. 5,119,831, which provides no fixed mean of patient registration. The clinician simply holds onto a tube placed into the patient's mouth, which has a pressure sensing bulb at its extreme end, that the patient compresses against another body part.

The IOWA Oral Performance Instrument is one of the few devices to be commercially available and it has been studied by numerous authors. In clinical practice it is most often used to measure the pressure an individual can exert against the roof (hard palate) of the patient's mouth. However, the company also sells what it calls a "lateral tongue bulb holder", which is a rigid stick to which the measurement bulb can be adhered. Once adhered, the patient then bites down on the stick to create a registration point for side-to-side (lateral) and sticking out the tongue (protrusion) measurements. Therefore, for lateral and protrusion measurements the patient is required to not only push against the bulb but to simultaneously bite down to keep the device in place, just as would be required with Durke's device previously mentioned.

Therefore, in order to obtain an accurate measurement of tongue strength all of the present devices require the patient to be registered to the device. This very act of patient registration requires clinicians to change their current clinical practice. Thus there is a continuing need for body force measurement systems that provide accurate quantifiable data that does not require clinicians to modify their clinical practice.

SUMMARY OF THE INVENTION

The above noted problems, and others, are overcome by the force sensing tongue depressor of this invention. It comprises a tongue depressor with a force sensing element attached to it that is either one-time-use pressure sensitive film or capable of being connected to measurement equipment.

DRAWINGS

Figures

DRAWING REFERENCE NUMBERS 100 force sensing tongue depressor
112 force sensing element
114 traces
120 measurement equipment
121 display mechanism
123 reset switch
125 battery door
127 operating mode switch
129 illumination switch
200 mechanical lock
210 lock engagement
300 ShuntMode Assembly
310 force-sensing ink
320 conductive electrode fingers
350 ThruMode Assembly
410 pre-conditioning circuit
420 peak detection circuit
430 display circuit

DETAILED DESCRIPTION

Figure 1:
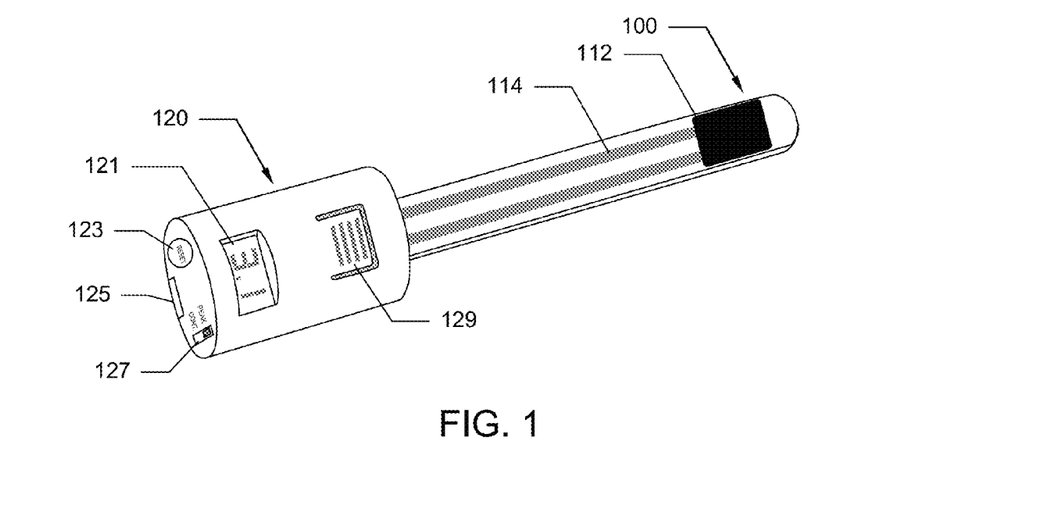
FIG. 1 is a perspective view of the first embodiment.

The first embodiment is illustrated in FIG. 1. This embodiment is comprised of a force sensing tongue depressor 100 and measurement equipment 120.

The force sensing tongue depressor 100 is a longitudinal element with a distal end of geometry similar to a standard tongue depressor and is comprised of a force sensing element 112 and traces 114. The force sensing element 112 is shown as a force sensing resistor. However, any element, or combination of elements, such as a force-sensing capacitors, strain gauges, liquid filled bladders with a pressure transducer and one-time-use pressure sensitive films are also options. Additionally, the force sensing tongue depressor 100 may optionally be covered by a disposable sheath, not shown.

The traces 114 are shown as conductive electrical traces however they should be viewed as representing the most appropriate manner of transmitting the information sensed by force sensing element 112 to the measurement equipment 120.

The force sensing element 112 will either be supplied attached to the force sensing tongue depressor 100 or attached by the clinician. The methods of attachment comprise the use of peel-and-stick adhesive, solvent bonding, ultrasonic welding, and/or laser welding.

The measurement equipment 120 is comprised of internal circuitry (not shown in this figure/see FIG. 4), a display mechanism 121, a reset switch 123, a battery door 125 and an operating mode switch 127. Additionally, and an optional illumination switch 129 is shown which would activate an illumination device (not visible) for the purpose of illuminating the end of the force sensing tongue depressor 100. The measurement equipment could either be a hand-held device (as shown), a component of a computer based system, or a separate system.

The operating mode switch 127 (as shown) is comprised of two modes: "Cont.", which would be utilized to provide continuous feedback of the level of force measured, and "Peak", which would be utilized to provide the value of the maximum force measured. However, additional modes related to specific exercise goals and or methods of communicating the level of force measured are also anticipated.

The display mechanism 121 is comprised of an LCD display with numeric characters. However, additional output modes such as graphical and/or auditory (including speech) are also anticipated.

Figure 2A:
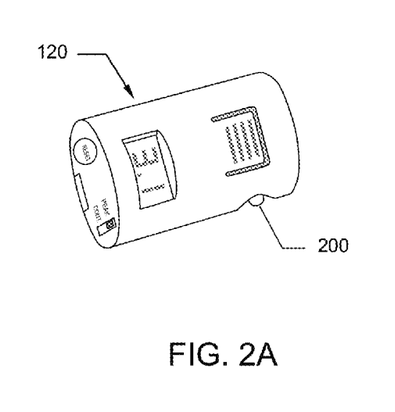
FIG. 2A to 2B shows the addition of a mechanical lock.

FIG. 2A shows the measurement equipment 120 as a separate unit, with an optional mechanical lock 200 included.

Figure 2B:
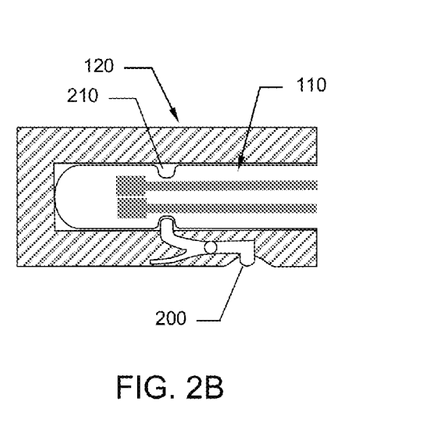

FIG. 2B shows a cross section view of the measurement equipment 120, in order to expose the mechanical lock 200, with the addition of the force sensing tongue depressor 100 inserted into it. Depending on the design of the mechanical lock 200, the force sensing tongue depressor 100 may or may not require a lock engagement 210. The purpose of the mechanical lock 200 is such that once engaged the force sensing tongue depressor 100 cannot be unintentionally removed.

Figure 3A:
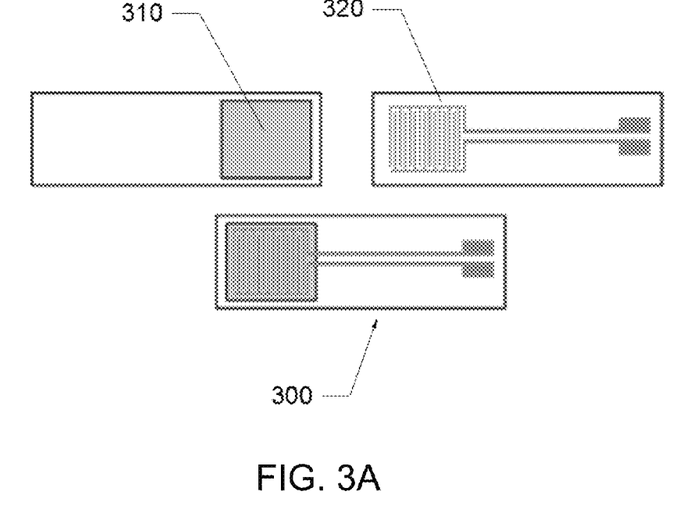
FIG. 3A to 3B shows methods of force sensing resistor construction.
Figure 3B:
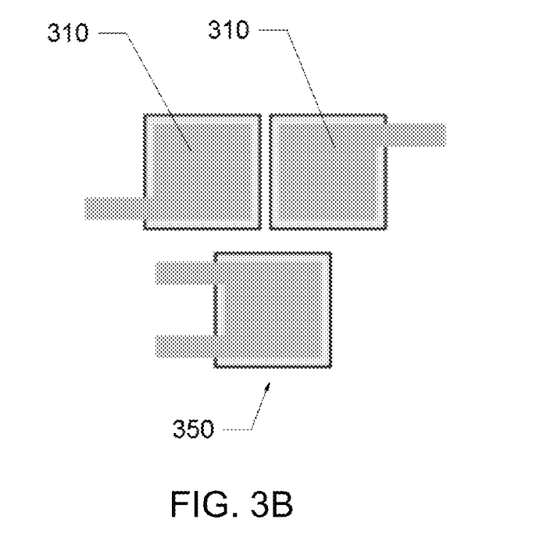

FIGS. 3A and 3b show typical construction methods of a force sensing resistor (FSR).

FIG. 3A shows the most common method of construction of the FSR, called, "ShuntMode". This method of assembly is constructed with two substrate layers, commonly of polyester film. One layer is coated with a proprietary force-sensing ink 310. The other substrate layer is screen printed with interdigitated conductive electrode fingers 320. The two substrates are then positioned facing each other (and typically adhered together with a double sided adhesive, which also serves as a spacer around the perimeter of the two substrates).

The interdigiting conductive fingers 320 can be manufactured in various ways. They can be screen printed on a substrate such as polyester film with silver or silver/graphite conductive ink, or etched in copper and gold plated on a printed circuit board. When a force is applied to the device, the shunt or shorting circuit is complete. The more force applied, the more conductive the output.

FIG. 3B shows an alternate method of constructing the FSR, the "ThruMode". It is also constructed with two layers of substrate such as polyester film. However in this case proprietary force-sensing ink 310 is then screen printed on each of the two substrates. In a similar manner, the two printed substrates are then placed facing each other. Adhesive can likewise be used to laminate the two substrate layers together. Similarly, the more force applied to the FRS, the more conductive the output.

Figure 4:
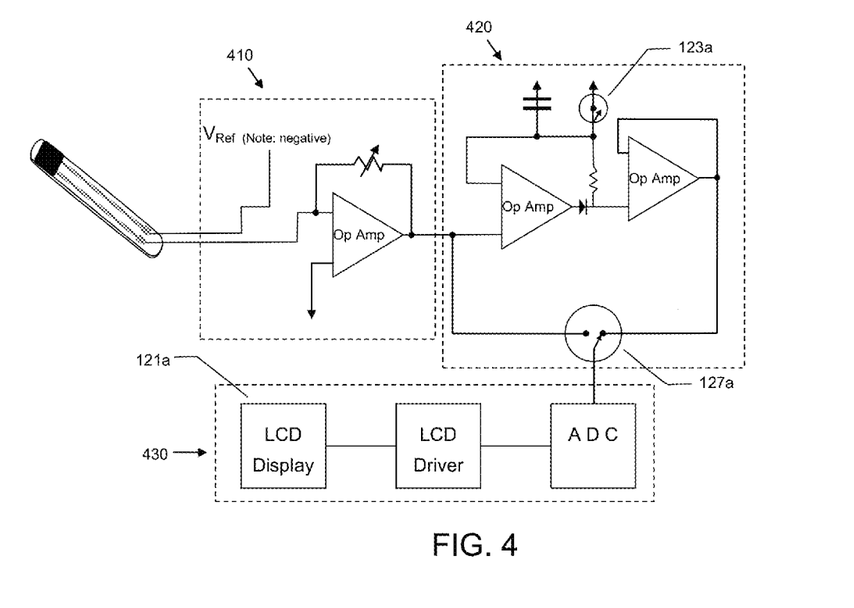
FIG. 4 is a schematic diagram.

FIG. 4 shows the schematic representation, using discrete components, comprising the internal circuitry of the measurement equipment 120 shown in FIG. 1. The schematic representation of the display mechanism 121, the reset switch 123, and the operating mode switch 127 of FIG. 1 are shown as a display mechanism 121a, a reset switch 123a, and an operating mode switch 127a of FIG. 4, respectively.

The internal circuitry is comprised of a pre-conditioning circuit 410, a peak detection circuit 420, and a display circuit 430. Additionally, the ability to provide a zero offset voltage as an input to the display circuit 430 is anticipated but not shown. The internal circuitry can either be discrete components (as displayed), microprocessor based, or software based (provided there is appropriate input to a computer, such as a USB port).

Figure 5:
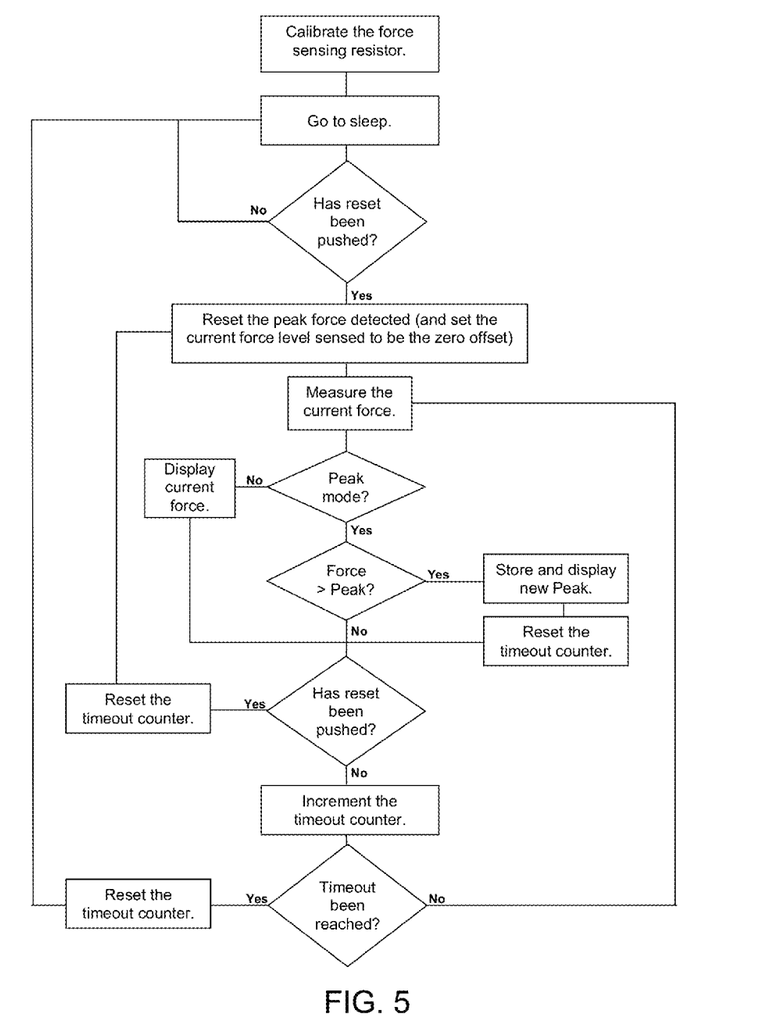
FIG. 5 is a flow diagram.

FIG. 5 is a flow diagram for the computer code for a microprocessor based implementation of the measurement equipment 120 shown in FIG. 1. The first step would be to calibrate the force sensing element. For force sensing resistors, the methods comprise both single and multi-point calibration.

In order to conserve battery power, the device would normally be asleep. However, once the reset switch was pressed (or the tongue depressor was inserted into the device if they are separate units) the current peak force level would be cleared and optionally the current force level sensed would be taken as the zero offset level from which all subsequent force measurements would be taken.

When awake, depending on the setting of the operating mode switch 127 of FIG. 1, the device would either: continuously monitor and display the maximum peak force observed or it would continuously monitor and display the current force observed, until such time as the device times out or the reset switch 123 (FIG. 1), is activated.

Figure 6A:
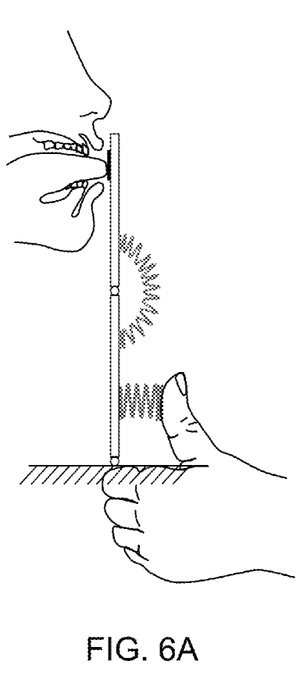
FIG. 6A to 6B shows a mechanical engineering representation.
Figure 6B:
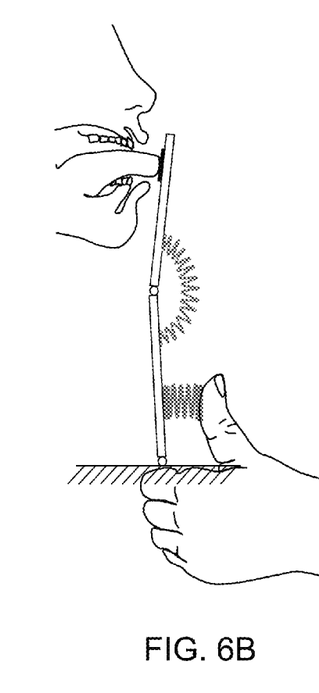

FIGS. 6A and 6B shows an engineering model of what occurs during tongue force measurement. The model represents the dynamic situation where the individual is causing a bend in the tongue depressor and the therapist is trying to hold the tongue depressor in place.

As long as the tongue depressor is not rigid, the system will achieve "measurement" equilibrium at the point the maximum tongue force is applied. The tongue force applied will be equal and opposite to the combination of bending of the tongue depressor and the stabilizing forces applied by the therapist.

Therefore, in trying to stabilize the measurement device, if one therapist causes a minor rotation on the tongue depressor and another does not then it will not impact the measurement, as "measurement" equilibrium is being approached. From an engineering standpoint, all it will do is cause a slight change in the angle of applied force that will not significantly change the results, due to the fact that the tongue depressor is relatively long in relationship to the deflection.

However, is should be noted that once "measurement" equilibrium has been achieved then the therapist can have an impact. Forces applied by the therapist (or by the patient pushing with their head, rather than their tongue) will be transmitted to the interface between the tongue and the depressor.

Fortunately, the force applied by the therapist will only be a fraction of the force as measured at the interface of the tongue due to the relative position of the applied force. Not only will the force applied by the therapist be reduced but it will be also be dampened by the additional bending of the depressor, assuming it is non-rigid.

Therefore, in order to reduce the risk of the therapist influencing the measurement, the depressor should be as flexible as possible. However, increased flexibility comes at the expense of tactile feedback and the two competing features need to be balanced. Additionally, to reduce the potential for the therapists to influence the measurement the following methodology is recommended. The therapist will ask the patient to stick out their tongue as hard as they can for a three count (1, 2, 3) and then relax. As such, the likelihood that the therapist will go much beyond the point of exceeding equilibrium will be minimized.

From the foregoing description, it can be seen that the present invention provides convenient method and system for making body force measurements consistent with current clinical practice and without the need for a fixed registration point.

It should be recognized, however, by those skilled in the art, that changes or modifications may be made to the above-described embodiments without departing from the broad inventive concepts of the invention. It should be understood, therefore, that the present invention is not limited to the particular embodiments disclosed herein, but is intended to cover all modifications and changes which are within the scope and spirit of the appended claims.

What is claimed is:

1. A force sensing tongue depressor comprising:
  a. a longitudinal element having a distal end with said distal end being a single flexible flat rectangular plate with a rounded tip
  b. a force sensing element located at the distal end of said longitudinal element
  c. traces that are used to transmit the information sensed by said force sensing element to measurement equipment
  and said force sensing tongue depressor is designed to achieve measurement equilibrium during the measurement of tongue force.

2. The force sensing tongue depressor of claim 1 wherein the force sensing element is comprised of a force sensing resistor, force-sensing capacitors, strain gauges, liquid filled bladders with a pressure transducer or one-time-use pressure sensitive films.

3. The force sensing tongue depressor of claim 1 includes measurement equipment capable of measuring and displaying said information sensed.

4. The force sensing tongue depressor of claim 3 wherein the measurement equipment includes the ability to establish a zero offset against which all force measurements are taken.

5. The force sensing tongue depressor of claim 3 comprises the ability of the measurement equipment to go to sleep when the longitudinal element is removed from said measurement equipment.

6. The force sensing tongue depressor of claim 3 further comprises a light capable of illuminating the distal end of the longitudinal element.

7. The force sensing tongue depressor of claim 3 wherein the measurement equipment further comprises a locking mechanism for the longitudinal element, such that said longitudinal element cannot be unintentionally removed.

8. The force sensing tongue depressor of claim 3 wherein the measurement equipment further comprises the ability to display peak force measured.

9. The force sensing tongue depressor of claim 1 wherein said longitudinal element is flexible and specifically designed such that tradeoff between flexibility and tactile feedback is optimized in order to reduce the risk of a therapist influencing the measurement of said information sensed, since decreased flexibility increases the risk that the therapist will influence the measurement of said information sensed while increased flexibility comes at the expense of tactile feedback and the two competing features need to be balanced.

10. A force sensing tongue depressor comprising:
  a. a longitudinal element having a distal end with said distal end being a single flexible flat rectangular plate with a rounded tip
  b. a force sensing element located at the distal end of said longitudinal element
  c. said force sensing element is a one-time-use pressure sensitive film and said force sensing tongue depressor is designed to achieve measurement equilibrium during the measurement of tongue force.

\* \* \* \* \*